United States Patent [19]
Reynolds

[11] Patent Number: 5,967,144
[45] Date of Patent: Oct. 19, 1999

[54] DISPOSABLE HEAD AND NECK IMMOBILIZATION DEVICE AND METHOD INCLUDING TUBE RETAINER

[76] Inventor: Connell Reynolds, 7855 Hobgood Rd., Fairburn, Ga. 30213

[21] Appl. No.: 09/056,011

[22] Filed: Apr. 6, 1998

Related U.S. Application Data

[63] Continuation-in-part of application No. 08/804,059, Feb. 21, 1997, Pat. No. 5,785,058.

[51] Int. Cl.$^6$ .................................................. A61B 19/00
[52] U.S. Cl. ............................... 128/869; 128/870; 5/637
[58] Field of Search ..................................... 128/845, 846, 128/869, 870; 5/636–645

[56] References Cited

U.S. PATENT DOCUMENTS

| | | | |
|---|---|---|---|
| 4,504,050 | 3/1985 | Osborne | 5/637 |
| 4,655,206 | 4/1987 | Moody | 128/870 |
| 5,435,323 | 7/1995 | Rudy | 128/870 |
| 5,588,445 | 12/1996 | Obaidi | 128/870 |

Primary Examiner—Michael A. Brown
Attorney, Agent, or Firm—Thomas, Kayden, Horstemeyer & Risley

[57] ABSTRACT

A disposable head and neck immobilization device allows the immobilization of a patient's head and neck, after the patient has been placed upon a spine board, without manipulating the patient's head and neck. The rugged denier nylon construction affords strength, comfort and durability, and allows for the adhesive free retention of a medical supply tube in the vicinity of the patients face. The immobilization device can be manufactured economically as to allow the device to be disposable, thus reducing contamination hazard from transfer of bodily fluids.

17 Claims, 6 Drawing Sheets

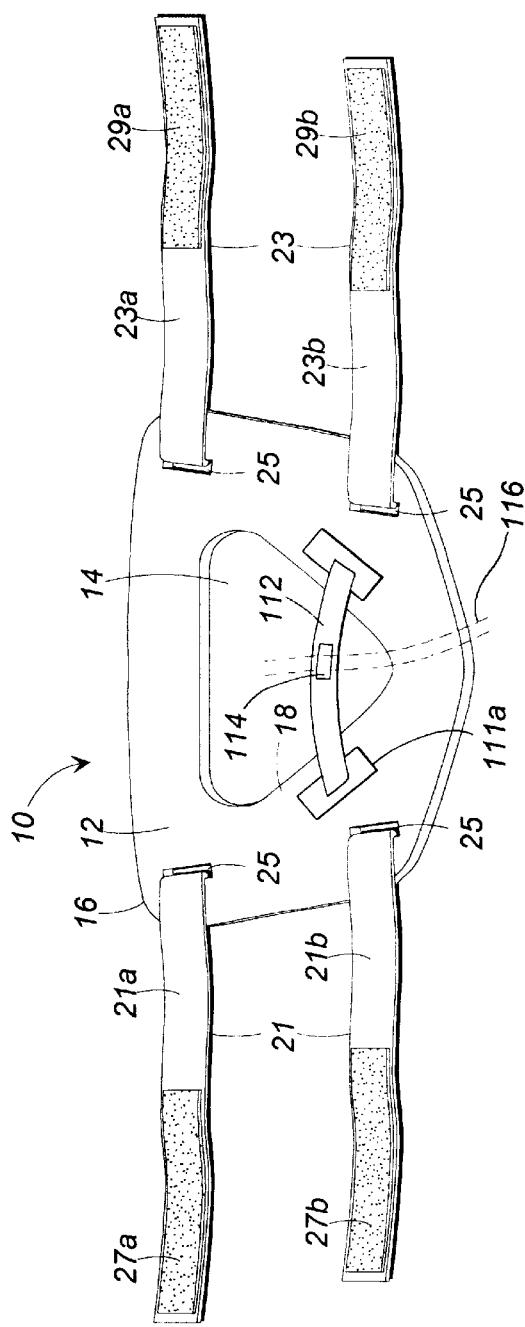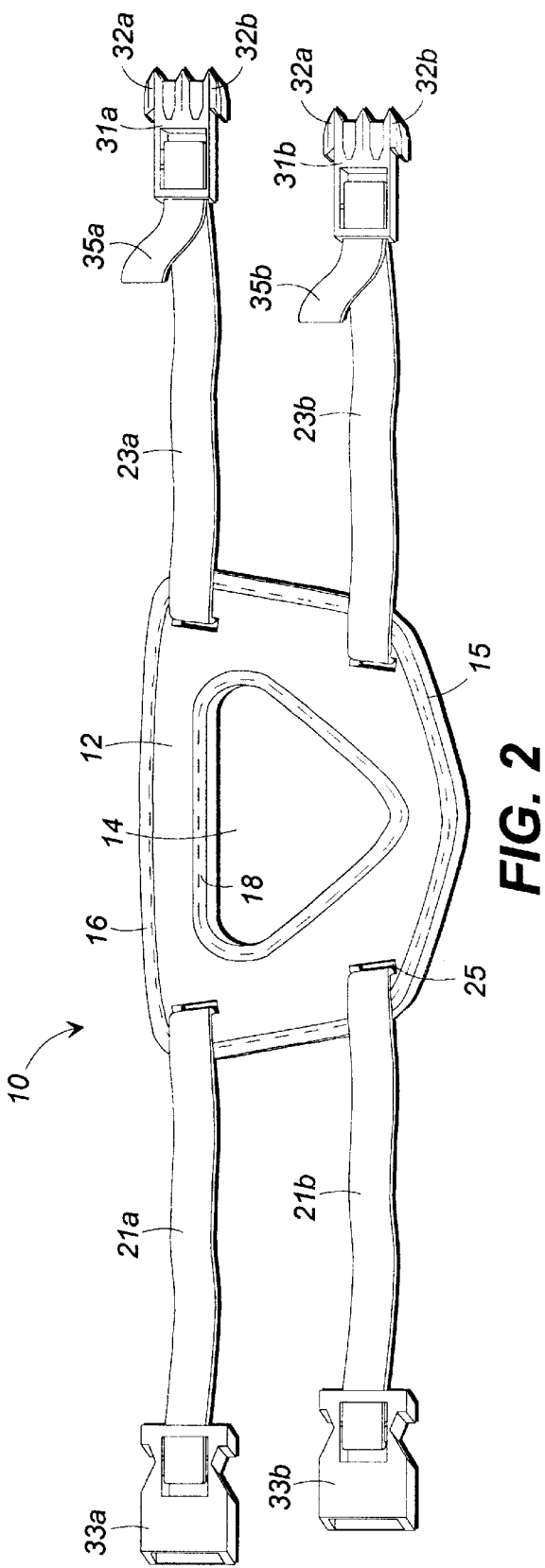

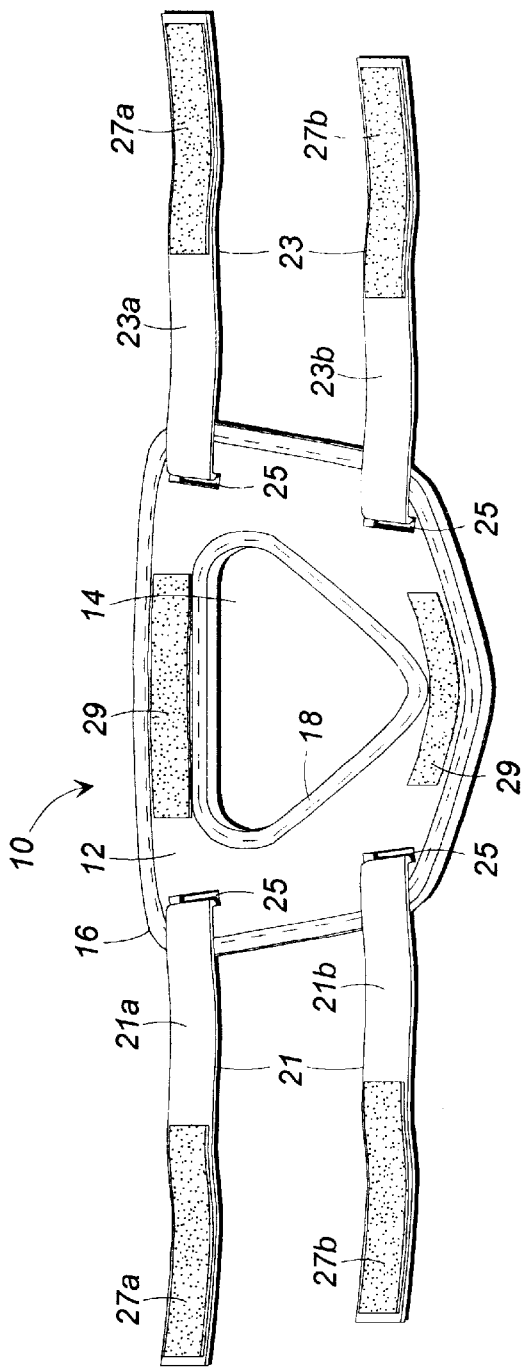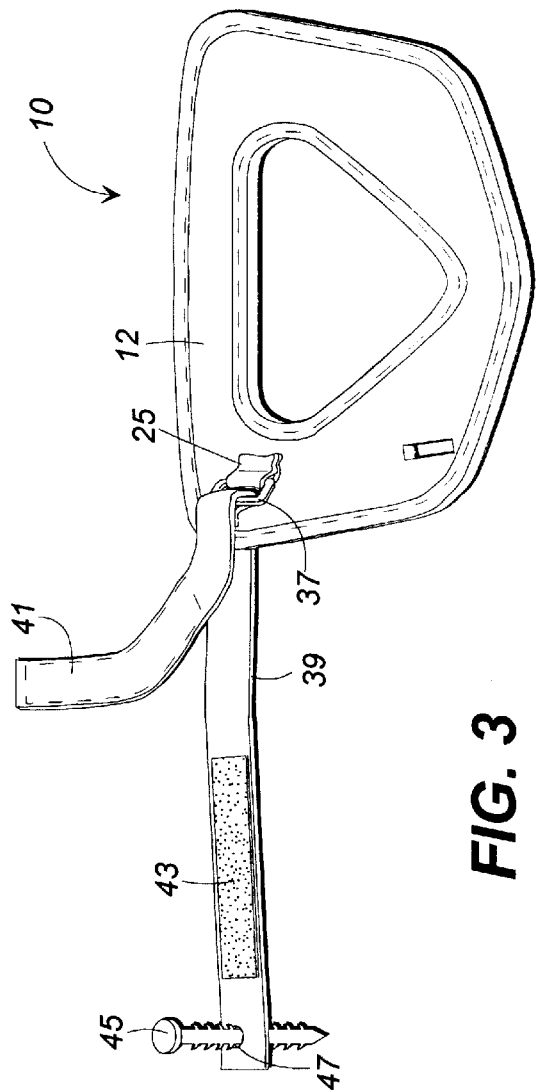

DISPOSABLE HEAD AND NECK IMMOBILIZATION DEVICE AND METHOD INCLUDING TUBE RETAINER

CROSS REFERENCE TO RELATED APPLICATION

This application is a continuation-in-part of and claims, for the common subject matter, priority to and the benefit of the filing date of co-pending patent application entitled DISPOSABLE HEAD AND NECK IMMOBILIZATION DEVICE AND METHOD, assigned Ser. No. 08/804,059, and filed Feb. 21, 1997, incorporated herein by reference.

FIELD OF THE INVENTION

The present invention relates generally to medical emergency equipment, and more particularly, to a disposable head and neck immobilization device including a tube retainer.

BACKGROUND OF THE INVENTION

In medical emergencies and accidents it is often necessary to immobilize a victim or patient prior to transporting the victim to a medical facility. Typically, a patient is placed on an immobilization board, known as a spine board, which maintains the patient in a flat, straight position. Additionally, in order to prevent further injury, the patient's head and neck must be further immobilized, typically by securing the patient's head to the spine board. Prior art devices are complex in design, difficult to apply and remove, and costly to manufacture. For example, the cervical collar disclosed in U.S. Pat. No. 4,043,325, which wraps around a patients neck, requires that the patients head be manipulated in order to secure the collar around the patients neck which can cause further, often irreparable injury in some cases. In most injury cases, one of the most important steps to be taken is the quick and safe immobilization of the patient. If immobilization requires manipulation of the patient's head and/or neck, then the goal of quick and safe immobilization is not realized. Similarly, the emergency neck immobilizer disclosed in U.S. Pat. No. 4,732,144 requires that the patient be manipulated in order to apply the device, and is complex in design and costly to manufacture. While these devices may help to immobilize a patient, they are cumbersome and uncomfortable, and may add to the feeling of anxiety being experienced by the patient, by being overly restrictive. Furthermore, these prior art devices are not designed to be disposable, and therefore, must be sterilized after each use. This presents a hazard of contamination from various bodily fluids and presents an increased health risk.

The prior art fails to provide an economical, sturdy, disposable head and neck immobilization device that is easy to apply and remove, and that allows the patient a decreased level of anxiety by allowing the patient to see and hear what is happening around them, and allowing the patient the ability, if able, to communicate freely with emergency personnel.

SUMMARY OF THE INVENTION

The present invention provides for a disposable head and neck immobilization device including a tube retainer. The disposable head and neck immobilization device can be of one piece construction and is preferably produced from new and innovative materials such as 950 Denier Ansotex manufactured by Allied Signal Corporation and cross linked polyethylene This allows the immobilization device of the present invention to be light in weight, while providing superior strength. The facepiece of the immobilization device of the present invention has a triangular shaped cutout designed to allow a substantial portion of a patient's face to remain uncovered, thus producing for the patient a decreased feeling of anxiety. Because the patients face and ears are not obstructed, they are, if able, free to communicate with emergency personnel. In one preferred embodiment, the facepiece is manufactured without any trim or finish detail, keeping cost as low as possible. In all embodiments described hereinafter, the head and neck immobilization device also includes a tube retainer designed to retain a medical supply tube in the vicinity of a patients face.

In a second preferred embodiment, the facepiece is manufactured with finish trim and piping in order to increase patient comfort.

The immobilization device as disclosed herein has four preferred embodiments for securing the device around the patients head, while the patient is lying in position on the spine board. In two preferred embodiments, a number of straps connected to the facepiece are passed through the spine board and fastened together on the lower, or underside, of the spine board, thus allowing the facepiece to exert pressure against a patients face in order to secure the patients head and neck to the spine board. Either a hook and loop fastening mechanism, or a releasable clip mechanism is used. In a third preferred embodiment, a number of straps are affixed to the spine board via a number of removable nylon pins. The opposite ends of the straps are threaded through fixtures secured to the facepiece. The straps are then tightened and secured with a hook and loop fastening mechanism. In a fourth preferred embodiment, a number of straps are fastened to a number of clips that are attached to the spine board.

The invention has numerous advantages, a few of which are delineated hereafter, as merely examples.

An advantage of the disposable head and neck immobilization device is that it allows a patient to be immobilized while still allowing communication with emergency personnel and a reduced level of anxiety imparted to the patient, and requires virtually no manipulation of the patient's head while being placed on his or her head.

Another advantage of the present invention is that it provides for the retention of a tube in the vicinity of the patients face while eliminating the need for adhesive tape.

Another advantage of the present invention is that it is constructed of new and innovative materials allowing one piece construction, light weight and superior strength.

Another advantage of the present invention is that it allows simplified application and removal from a patient.

Another advantage of the present invention is that it is disposable, thus decreasing health and safety risk by reducing or eliminating the risk of contamination from bodily fluids.

Another advantage of the present invention is that it is simple in design, reliable in operation, and economical to manufacture.

Other objects, features, and advantages of the present invention will become apparent to one with skill in the art upon examination of the following drawings and detailed description. It is intended that all such additional objects, features, and advantages be included herein within the scope of the present invention, as defined in the appended claims.

BRIEF DESCRIPTION OF THE DRAWINGS

The present invention, as defined in the claims, can be better understood with reference to the following drawings.

3

The drawings are not necessarily to scale, emphasis instead being placed on clearly illustrating the principles of the present invention.

Figure 1B:
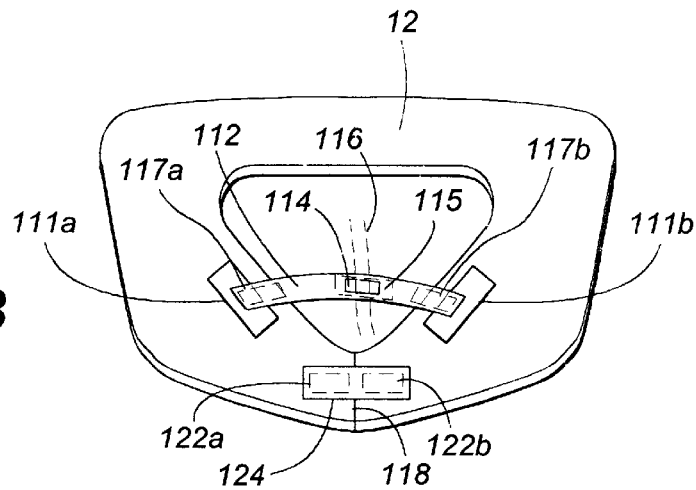

FIG. 1A is a view of a first embodiment of the head and neck immobilization device of the present invention;

FIG. 1B is a detail view illustrating the tube retainer and slit of the head and neck immobilization device of FIG. 1A;

FIG. 2 is a view of a second embodiment of the head and neck immobilization device of the present invention;

FIG. 2A is a view of a third embodiment of the head and neck immobilization device of the present invention.

Figure 4:
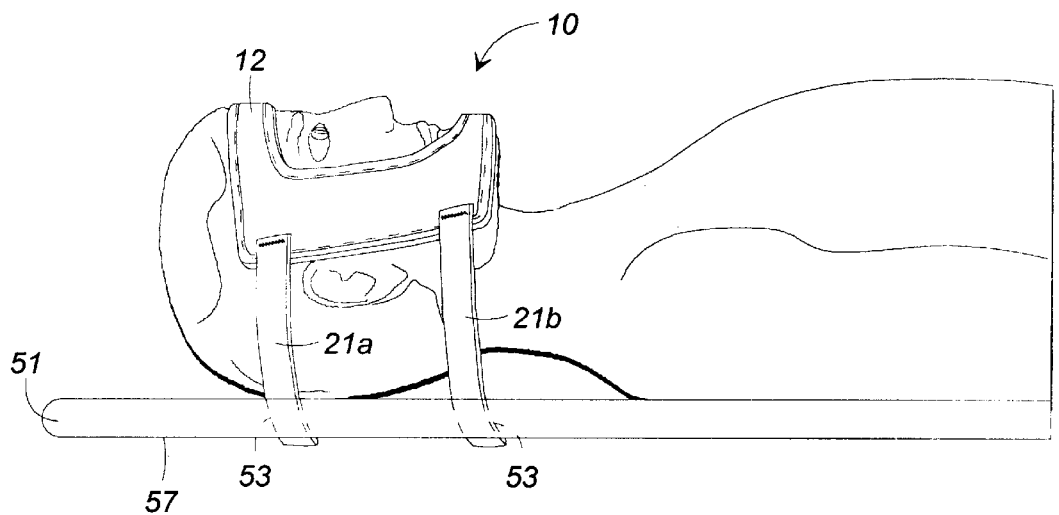
Figure 5:
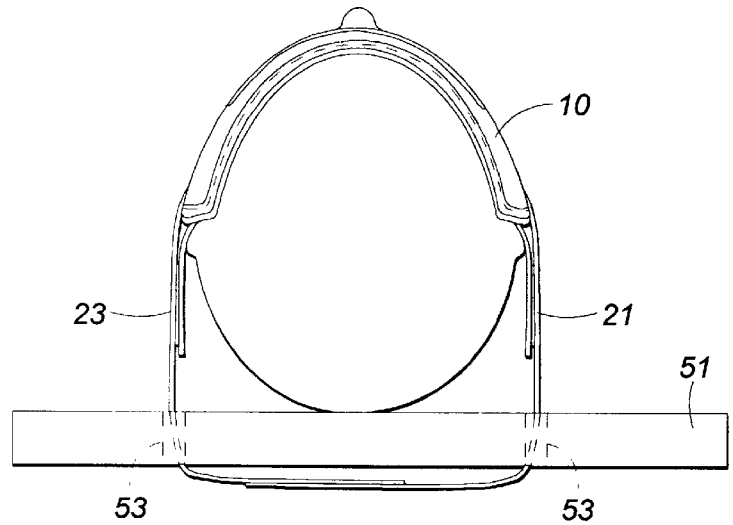
Figure 6:
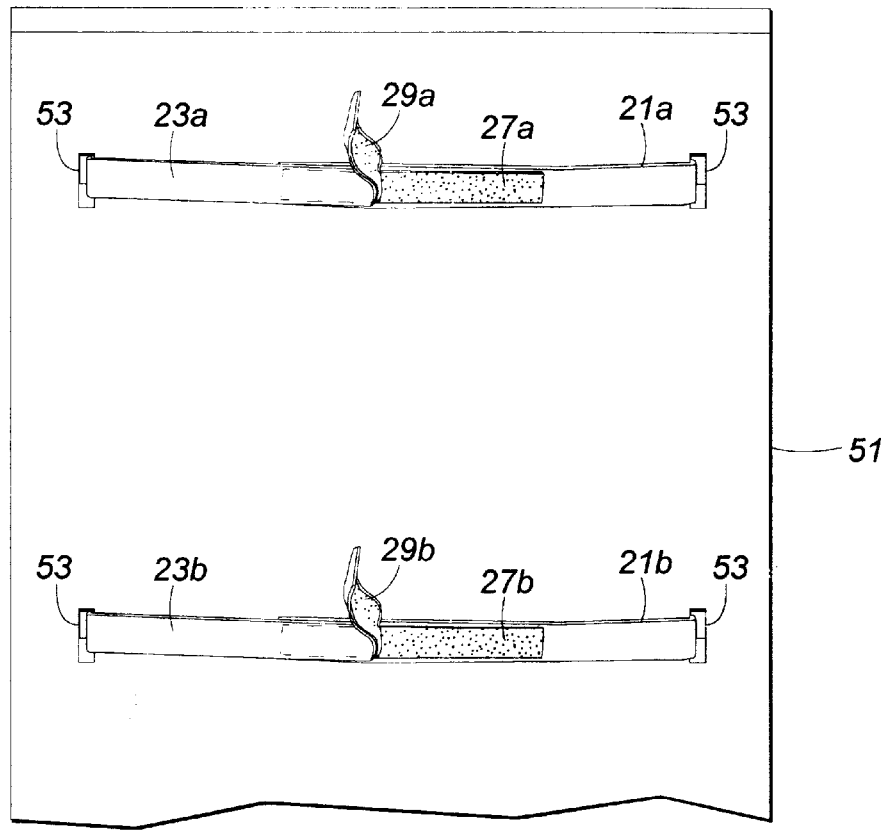
Figure 7:
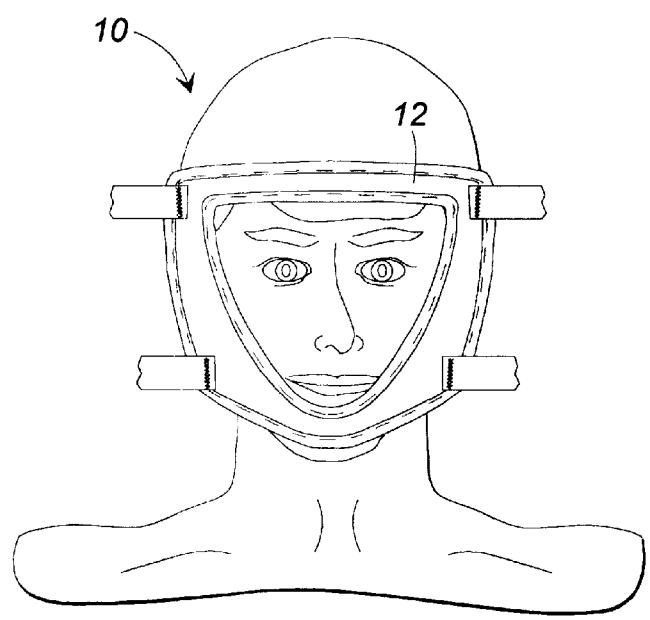
Figure 8:
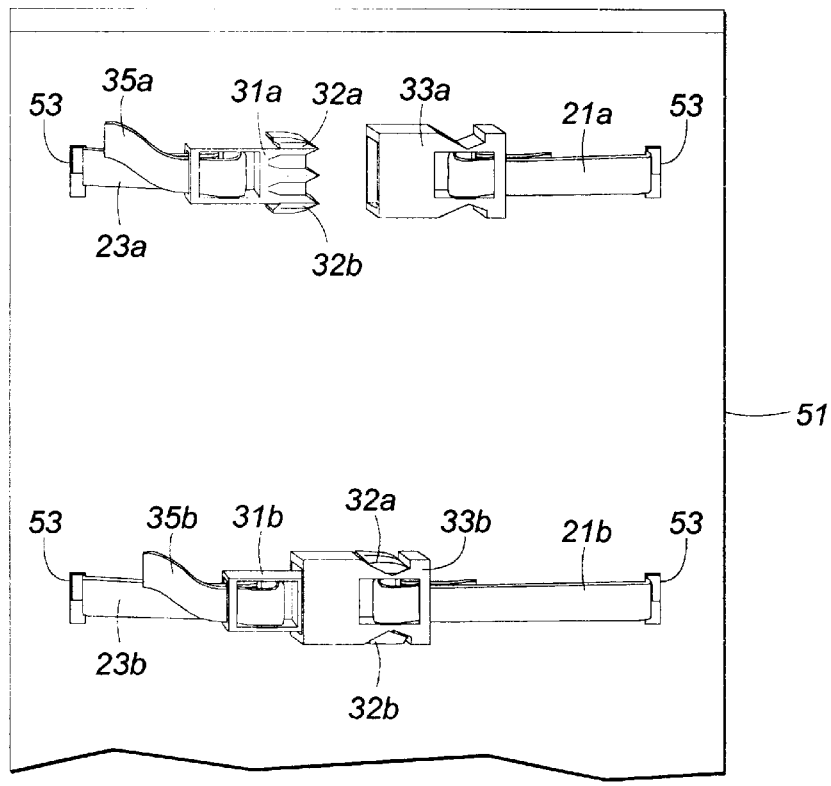
Figure 9:
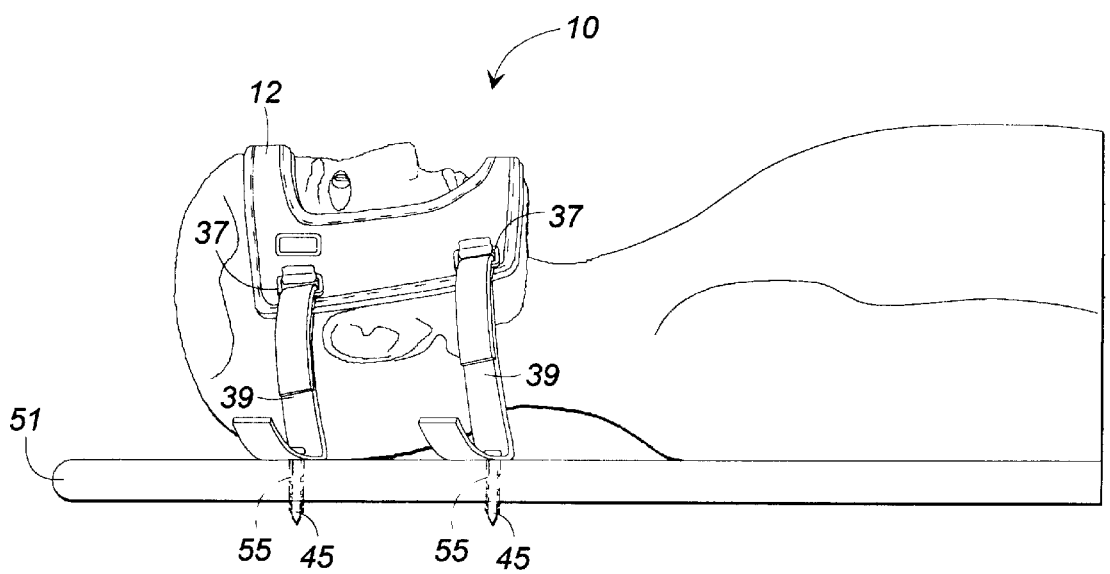
Figure 10:
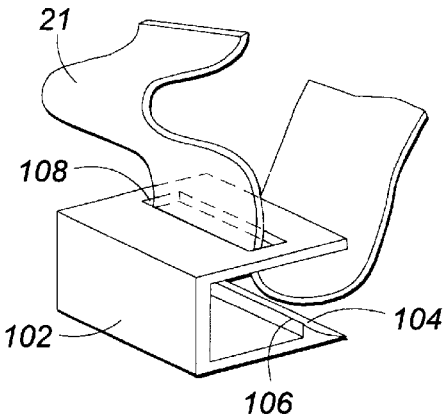
Figure 11:
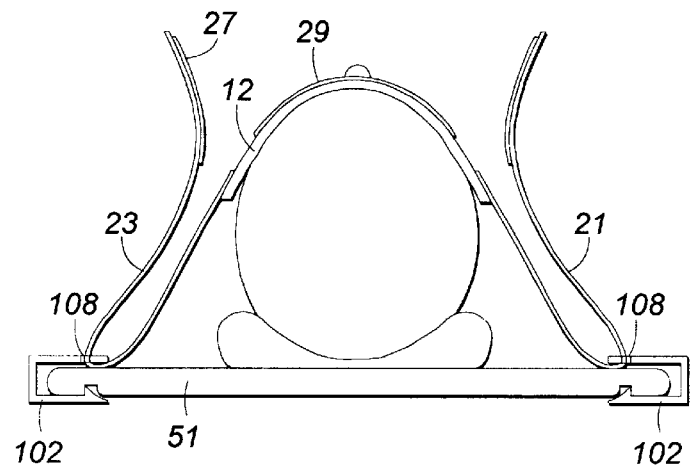
Figure 12:
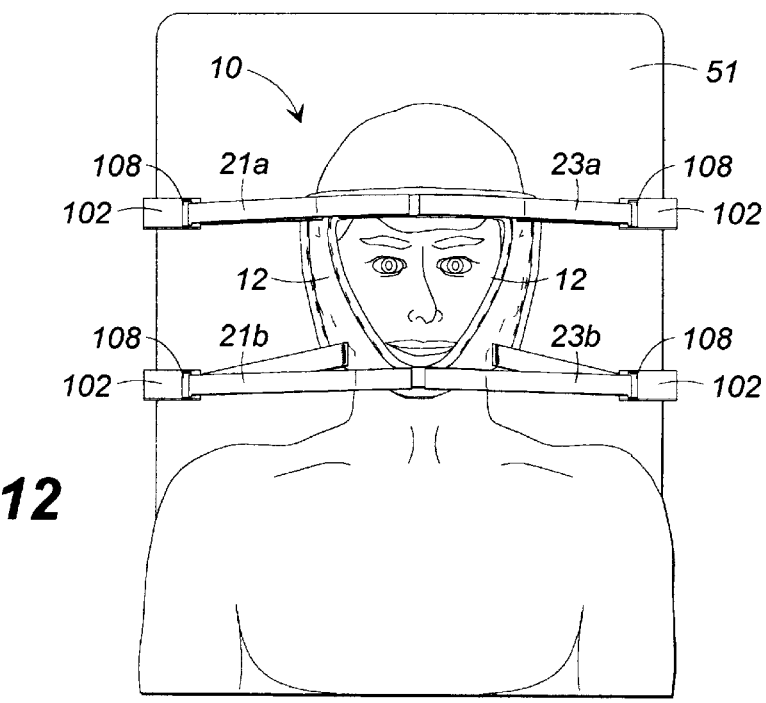

FIG. 3 is a detail view of a fourth embodiment of the head and neck immobilization device of the present invention;

FIG. 4 is a profile view of the immobilization device of FIGS. 1 or 2 as applied to a patient;

FIG. 5 is an end view of the immobilization device of FIGS. 1 or 2 as applied to a patient;

FIG. 6 is a detail view illustrating the closure means of the immobilization device of FIG. 1;

FIG. 7 is a frontal view of all embodiments of the immobilization device of the present invention as applied to a patients face;

FIG. 8 is a detail view illustrating the closure means of the immobilization device of FIG. 2;

FIG. 9 is a profile view of the immobilization device of FIG. 3 as applied to a patient;

FIG. 10 is a detail view of the attachment clip of the immobilization device of FIG. 2A, FIG. 11 is an end view of the immobilization device of FIG. 2A as applied to a patient; and FIG. 12 is a frontal view of the immobilization device of FIG. 2A as applied to a patients face.

DETAILED DESCRIPTION OF THE PREFERRED EMBODIMENT

Referring to FIG. 1, there is shown a view of one embodiment of the head and neck immobilization device 10 of the present invention. Facepiece 12 is designed with a triangular shaped opening 14 that leaves a large portion of a patient's face unobstructed, such that when the immobilization device 10 is applied, the patient does not feel claustrophobic or overly restrained and if able, he or she can readily communicate with emergency personnel. Facepiece 12 is shown in one embodiment in FIGS. 1A and 1B having edges 16 and 18 unfinished in order to minimize production cost and maximize economy. FIG. 2, depicting an alternate embodiment of facepiece 12, shows edges 16 and 18 finished with trim piping 15 and 20 in order to maximize comfort for the patient. Additional embodiments of the facepiece are envisioned without departing from the inventive concept of the present invention. Also shown in FIGS. 1A and 2 are straps 21 and 23, which will be discussed in detail hereafter.

Applicable to all embodiments, but shown with respect to FIGS. 1A and 1B for simplicity, is tube retainer 112. Tube retainer 112 is designed to releasably fasten to facepiece 12 using, for example, hook and loop fastener means such as Velcro™. For example, hook portions 111a and 111b can be fastened to facepiece 12. Loop portion 117a and 117b can be fastened to the underside of tube retainer 112. When applied to facepiece 12, tube retainer 112 can retain tube 116 using tube retainer means 114, which can illustratively be an additional piece of hook and loop fastening material. That is, means 114 can be illustratively a strip of material or indeed, can be a hook portion of hook and loop fastening mechanism. Loop portion 115 may illustratively be attached to tube retainer 112, whereby tube 116 is secured in place by placing strip 114 over tube 116 and onto loop portion 115.

Tube 116 may be retained in the vicinity of a patients face without the need for fastening the tube to the patient using, for example, an adhesive tape, thereby more comfortably enabling a patient to receive medical care. While described with reference to head and neck immobilization device 10 shown in FIGS. 1A and 1B, tube retainer 112 is applicable to all embodiments of the head and neck immobilization device described herein.

Also applicable to all embodiments, but illustrated with respect to FIG. 1B for simplicity, is an alternate embodiment of the facepiece whereby facepiece 12 is equipped with slit 118. Slit 118, located on the lower portion of facepiece 12 allows is head and neck immobilization device 10 to be more easily removed from a patient. Upon application of head and neck immobilization device 10 to a patient, slit 118 is held together using, for example, hook and loop fastening means 122 and 124. For example, hook portion 122a and 122b may be securely fastened to facepiece 12. Slit 118 can be held together by applying strip 124, which may illustratively be the loop portion of a hook and loop fastening means. In this manner, facepiece 12 remains intact for application over the face of a patient, however, by removing strip 124, thereby allowing the separation of facepiece 12 at slit 118, head and neck immobilization device 10 can more easily be removed.

First Embodiment

Referring again to FIG. 1A, there is shown a view of a first embodiment of the head and neck immobilization device 10. Facepiece 12 can be either embodiment as discussed previously. For purposes of this discussion, the economy embodiment of facepiece 12 is illustrated. Securely fastened to facepiece 12 at appropriate locations 25, are straps 21 and 23. Straps 21 and 23 are of sufficient cross section so as to fit through a corresponding opening in a spine board such as the Ultra-Loc™ Backboard manufactured by Fleming Industries Inc., and of sufficient length so as to extend through the above referenced spine board openings and emerge from the lower side of the spine board, and allow the straps to be fastened together as described hereafter. Straps 21a and 21b are manufactured with, for example, the loop portion 27a and 27b, respectively, of a hook and loop fastening mechanism (such as Velcro™) firmly attached thereto. Similarly, straps 23a and 23b are manufactured with the corresponding hook portion 29a and 29b, respectively, of a hook and loop fastening mechanism (such as Velcro™) firmly attached thereto. Loop portion 27 and hook portion 29 are attached to straps 21 and 23, respectively, in such a way as to allow the loop portion 27 to contact the hook portion 29 when straps 21 and 23 are inserted through the openings in a spine board, emerging from the lower side, thus allowing the secure fastening of strap 21 to strap 23.

Referring now to FIG. 4, shown is a profile view of the immobilization device as applied to a patient, illustrating the use of a first embodiment of immobilization device 10. Facepiece 12 is applied against a patients face after the patient has been placed upon spine board 51. Straps 21 and 23 (not shown in this view) are passed through corresponding openings 53 in spine board 51 so as to extend from the lower side 57 of spine board 51. FIG. 5 illustrates an end view of the immobilization device as applied to a patient. Referring now to FIG. 6, shown is a detail view illustrating the closure means of this embodiment. Straps 21 and 23 are inserted through openings 53 in spine board 51 and pulled snug on the lower side 57 of spine board 51. While immobilization device 10 is being held snugly against the patient, hook portion 29 of strap 23 is pressed against loop portion 27 of strap 21, thus releasably, but firmly securing the device over a patients head. Referring now to FIG. 7, shown is a frontal view of the immobilization device 10 applied to a patients face. As can be seen, facepiece 12 allows a substantial portion of a patients face to remain uncovered, thus minimizing the patients anxiety or feeling of oppressive confinement. In order to release immobilization device 10, loop portion 27 is separated from hook portion 29 by pulling apart, and straps 21 and 23 are released through openings 53 of spine board 51.

Second Embodiment

Referring now to FIG. 2, there is shown a view of a second embodiment of the head and neck immobilization device 10 of the present invention. Facepiece 12 can be either embodiment as discussed previously. For purposes of this discussion, the piping trimmed embodiment of facepiece 12 is illustrated. Securely fastened to facepiece 12 at appropriate locations 25, are straps 21 and 23. Securely fastened to the ends of straps 21a and 21b are the receptacle portions 33a and 33b, respectively, of a releasable clip mechanism. Slidably coupled to the free ends of straps 23a and 23b are the clip portions 31a and 31b, respectively, of a releasable clip mechanism. Receptacle portion 33 and clip portion 31 are of sufficient cross section so as to fit through a corresponding opening in a spine board such as that referenced above. Straps 21 and 23 are of sufficient length so as to extend through the above referenced spine board openings and allow straps to be fastened together on the lower side of the spine board as described hereafter.

The use of this embodiment of immobilization device 10 is similar to that described above with the exception of the strap closure means. Referring again to FIG. 4, facepiece 12 is applied against a patients face after the patient has been placed upon spine board 51. Straps 21 and 23 are inserted through corresponding openings 53 of spine board 51. Referring now to FIG. 8, shown is a detail view illustrating the closure means of this embodiment. Clip portion 31 of strap 23 and receptacle portion 33 of strap 21 are passed through openings 53 and extend through lower side 57 of spine board 51. Clip portion 31 is then releasably engaged to receptacle portion 33. Section 35 of strap 23 slidably extends through clip portion 31, allowing strap 23 to be snugly tightened to strap 21, by pulling section 35 of strap 23 through clip portion 31 until snug. In order to release immobilization device 10, inwardly depress release tangs 32 of clip portion 31 in order to separate clip portion 31 from receptacle portion 33.

Third Embodiment

Referring now to FIG. 2A, there is shown a view of a third embodiment of the head and neck immobilization device 10 of the present invention. Facepiece 12 can be either embodiment as discussed previously. For purposes of this discussion economy embodiment of facepiece 12 is illustrated. Securely fastened to facepiece 12 at approximate locations 25, are straps 21 and 23. Straps 21 and 23 are of sufficient cross section so as to fit through a corresponding opening in a clip attached to a spine board, and of sufficient length so as to loop through the clip and extend back to facepiece 12. Straps 21 and 23 are manufactured with, for example, the loop portion 27a and 27b respectively, of a kook and loop fastening mechanism (such as Velcro™) firmly attached thereto. Facepiece 12 is manufactured with the corresponding hook portion 29, of a hook and loop fastening mechanism (such as Velcro™) firmly attached thereto at approximate locations as shown. Loop portion 27 is attached to straps 21 and 23, and hook portion 29 is attached to facepiece 12 in such a way as to allow loop portion 27 to contact hook portion 29 when straps 21 and 23 are looped through a clip attached to the spine board.

Referring now to FIG. 10, there is shown the clip 102 used in this embodiment of the present invention. Clip 102 is designed as a C shaped member having aperture 104. Aperture 104 is designed to receive the thickness of the spine board. Clip 102 also has engagement barb 106 disposed to engage a corresponding recess in a spine board. Clip 102 also has aperture 108 designed to receive straps 21 and 23. For simplicity, only strap 21 is shown in FIG. 10.

Referring now to FIG. 11, there is shown an end view of the immobilization device as applied to a patient, illustrating the use of a second embodiment of immobilization device 10. Facepiece 12 is applied against a patients face after the patient has been placed upon spine board 51. Clips 102 are shown as applied to the spine board in approximate locations so as to receive straps 21 and 23 through apertures 108 of clips 102. Straps 21 and 23 are passed through apertures 108 of clips 102 and are looped and pulled snug. While immobilization device 10 is being held snugly against a patient loop portion 27 of straps 21 and 23 are pressed against hook portion 29, thus releasably but firmly securing the device over the patients head.

Referring now to FIG. 12, there is shown a frontal view of the immobilization device 10 applied to a patients face. As can be seen, facepiece 12 allows a substantial portion of a patients face to remain uncovered, thus minimizing the patients anxiety or feeling of oppressive confinement. In order to release immobilization device 10, strap 21 is separated from strap 23 by pulling apart, and straps 21 and 23 are released through apertures 108 in clips 102.

Fourth Embodiment

Referring now to FIG. 3, there is shown a view of a fourth embodiment of the head and neck immobilization device 10 of FIG. 1. Facepiece 12 can be either embodiment as discussed previously. For purposes of this discussion, the economy embodiment of facepiece 12 is illustrated. Securely fastened to facepiece 12 at appropriate locations 25, are fixtures 37. Fixture 37 allows the unobstructed passage of strap 39. Strap 39 is of sufficient cross section so as to slidably fit through fixture 37. Strap 39 is manufactured with the loop portion 41 of a hook and loop fastening mechanism (such as Velcro™), firmly attached thereto. Similarly, a hook portion 43 of a hook and loop fastening mechanism is firmly attached to an end opposite that to which the loop portion 41 is attached. Loop portion 41 and hook portion 43 are attached to the same surface of strap 39. Strap 39 contains a hole 47 at one end through which removable nylon pin 45 releasably, but snugly, passes. Removable nylon pin 45 is designed to be inserted into a corresponding bore in a spine board, thus securely fastening one side of strap 39 to the spine board.

Referring now to FIG. 9, there is shown a profile view of the immobilization device as applied to a patient, illustrating the use of a third embodiment. Facepiece 12 is applied against a patients face after the patient has been placed upon spine board 51. Now also referring to FIG. 3, removable nylon pin 45 is passed through hole 47 in strap 39 and inserted into corresponding bore 55 in spine board 51. The free end of strap 39 is passed through fixture 37, pulled gently snug, and secured by pressing loop portion 41 to hook portion 43. In order to release immobilization device 10, loop portion 41 is separated from hook portion 43 by pulling apart and releasing strap 39 through fixture 37.

In all of the above embodiments of the invention, the device is placed over the patient's head, bearing primarily against forehead and chin, and is applied in place by means of the straps. There is no manipulation of the patient's head and neck, presuming he is placed upon his or her back on the spine board, which is usually the case, hence the danger of further injury is eliminated.

It will be obvious to those skilled in the art that many modifications and variations may be made to the preferred embodiments of the present invention, as set forth above, without departing substantially from the principles of the present invention. For example, many iterations of the immobilization device are possible. For example, in applications where a disposable immobilization device is required, the device can be manufactured in order to maximize economy by omitting the facepiece trim and using hook and loop fasteners. In an application that demands increased ruggedness or comfort, the immobilization device can be fabricated with facepiece trim and a snap fit or pin attachment means. Furthermore, features can be mixed in order to satisfy any combination of economy, ruggedness and comfort, and furthermore, hook portions may be interchanged with loop portions without departing from the scope of the invention.

All such modifications and variations are intended to be included herein within the scope of the present invention, as defined in the claims that follow.

I claim:

1. A disposable head and neck immobilization device for use with an immobilization board having an upper side and a lower side, comprising:

a facepiece having a cutout portion therein for receiving a patient's face, and first and second side portions on either side of the cutout portion;

first and second fastening means located on said first and second side portions;

a tube retainer designed to releasably fasten to said first and second fastening means;

first and second straps each having a first and second end, said first end of each of said straps being connected to one of said side portions of said facepiece for securing said immobilization device over the head of a patient, and said second end of each of said straps being disposed to pass through an opening in the immobilization board; and attachment means for affixing said device on the immobilization board.

2. The device according to claim 1, wherein said first and second fastening means comprises a hook and loop type fastening mechanism, and said tube retainer has first and second ends, each of said ends having hook and loop type fastening means thereon for mating with said first and second fastening means.

3. The device according to claim 1, further comprising a slit in said facepiece, said slit between said first and second side portions.

4. The device according to claim 1, wherein said attachment means further comprises a releasable clip mechanism having a clip portion and a receptacle portion, whereby said clip portion is slidably coupled to said second end of said first straps and said receptacle portion is affixed to said second end of said second straps, and said clip portion releasably engages said receptacle portion allowing said second end of said second straps to adjustably slide within said clip portion allowing the fastening of said first straps to said second straps thereby tightening said facepiece securely against the head of an immobilized patient.

5. A disposable head and neck immobilization device for use with an immobilization board having a plurality of bores, comprising:

a facepiece having a cutout portion therein for receiving a patient's face, first and second side portions on either side of the cutout portion, and having a plurality of connectors affixed to said first and second side portions;

first and second fastening means located on said first and second side portions;

a tube retainer designed to releasably fasten to said first and second fastening means;

a plurality of straps each having a first and second end, said first end having a hole therein, and a hook portion of a hook and loop fastening system affixed thereto, and said second end having a loop portion of a hook and loop fastening system affixed thereto; and a removable nylon pin designed to pass through said hole in said first end of each of said plurality of straps, and adapted to securely engage a corresponding bore in the immobilization board, and said second end of each of said plurality of straps is slidably disposed through each of said connectors affixed to said first and second side portions of said facepiece whereby said hook portion engages said loop portion allowing the fastening of said facepiece securely against the head of an immobilized patient.

6. The device according to claim 5, wherein said first and second fastening means comprises a hook and loop type fastening mechanism, and said tube retainer has first and second ends, each of said ends having hook and loop type fastening means thereon for mating with said first and second fastening means.

7. The device according to claim 5, further comprising a slit in said facepiece, said slit between said first and second side portions.

8. A method for immobilizing the head and neck of a patient against an immobilization board having an upper side and a lower side, comprising the steps of:

placing a facepiece, having a cutout portion therein for receiving a patients face, first and second side portions on either side of the cutout portion, first and second fastening means located on said first and second side portions, first and second straps each having a first and second end, said first end connected to said first and second side portions of said facepiece, over the face of a patient;

inserting said second end of first and second straps through an opening in the immobilization board;

fastening together said first and second straps on the lower side of the immobilization board in order to immobilize the head and neck of a patient; and releasably fastening a tube retainer to said first and second fastening means.

9. The method according to claim 8, wherein said first and second fastening means comprises a hook and loop type fastening mechanism, and said tube retainer has first and second ends, each of said ends having hook and loop type fastening means thereon for mating with said first and second fastening means, wherein each of said ends is mated to one of said fastening means.

10. A method for immobilizing the head and neck of a patient against an immobilization board having a plurality of bores, comprising the steps of:

placing a facepiece having a cutout portion therein for receiving a patient's face, first and second side portions on either side of the cutout portion, first and second fastening means located on said first and second side portions, and having a plurality of connectors affixed to said first and second side portions, over the face of a patient, said plurality of connectors designed to allow the passage of a plurality of straps each having a first end and a second end, said first end having a hole therein and a hook portion of a hook and loop fastening system affixed thereto, and said second end having a loop portion of a hook and loop fastening system affixed thereto;

passing a removable nylon pin through said hole in a first end of each of said plurality of straps;

inserting said removable nylon pin into a corresponding bore in an immobilization board;

inserting said second end of each of said plurality of straps through each of said connectors affixed to said facepiece;

tightening said second end of each of said plurality of straps by pulling said second end through each of said connectors affixed to said facepiece and securing said second end of each of said plurality of straps to said first end of each of said plurality of straps thereby adjustably tightening said facepiece securely against the head of an immobilized patient; and releasably fastening a tube retainer to said first and second fastening means.

11. The method according to claim 10, wherein said first and second fastening means comprises a hook and loop type fastening mechanism, and said tube retainer has first and second ends, each of said ends having hook and loop type fastening means thereon for mating with said first and second fastening means, wherein each of said ends is mated to one of said fastening means.

12. A disposable head and neck immobilization device for use with an immobilization board, comprising:

a facepiece having a cutout portion therein for receiving a patient's face, first and second side portions on either side of the cutout portion, upper and lower portions above and below the cutout portion, and attachment means affixed to said upper and lower portions;

first and second fastening means located on said first and second side portions;

a tube retainer designed to releasably fasten to said first and second fastening means;

a plurality of clips designed to receive the edge thickness of the immobilization board;

first and second straps each having a first and second end, said first end of each of said straps being connected to one of said side portions of said facepiece for securing said immobilization device over the head of a patient, and said second end of each of said straps being disposed to pass through an opening in one of said plurality of clips; and attachment means for attaching said second ends to said facepiece.

13. The device according to claim 12, wherein said attachment means further comprises a hook and loop fastening mechanism, whereby a loop portion is affixed to said second end of said first straps and said second straps and a loop portion is affixed to said upper and lower portions of said facepiece and said hook portion is releasably fastened to said loop portion allowing the adjustable fastening of said first strap to said second strap tightening said facepiece securely against the head of an immobilized patient.

14. The device according to claim 12, further comprising a slit in said facepiece, said slit between said first and second side portions.

15. The device according to claim 12, wherein said first and second fastening means comprises a hook and loop type fastening mechanism, and said tube retainer has first and second ends, each of said ends having hook and loop type fastening means thereon for mating with said first and second fastening means.

16. A method for immobilizing the head and neck of a patient against an immobilization board, comprising the steps of:

placing a facepiece, having a cutout portion therein for receiving a patients face, first and second side portions on either side of the cutout portion, first and second fastening means located on said first and second side portions, upper and lower portions above and below the cutout portion, first and second straps each having a first and second end, said first end connected to said first and second side portions of said facepiece, and an attachment means affixed to said upper and lower portions, over the face of a patient;

inserting said second end of said first and second straps through an opening in each of a plurality of clips;

fastening said second end of said first and second straps to said upper and lower portions of said facepiece in order to immobilize the head and neck of a patient; and releasably fastening a tube retainer to said first and second fastening means.

17. The method according to claim 16, wherein said first and second fastening means comprises a hook and loop type fastening mechanism, and said tube retainer has first and second ends, each of said ends having hook and loop type fastening means thereon for mating with said first and second fastening means, wherein each of said ends is mated to one of said fastening means.

* * * * *